United States Patent [19]
Cicio

[11] Patent Number: 5,742,948
[45] Date of Patent: Apr. 28, 1998

[54] FEMALE URINATION AID

[76] Inventor: William H. Cicio, 305 Blacksmith Rd., Levittown, N.Y. 11756

[21] Appl. No.: 693,644

[22] Filed: Aug. 9, 1996

Related U.S. Application Data

[60] Provisional application No. 60/002,609, Aug. 11, 1995.
[51] Int. Cl.$^6$ ................................................ A47K 11/00
[52] U.S. Cl. .......................... 4/144.3; 4/144.4; 141/337
[58] Field of Search ......................... 4/144.1–144.4; 141/337, 340

[56] References Cited

U.S. PATENT DOCUMENTS

| | | |
|---|---|---|
| 1,510,973 | 10/1924 | Behan . |
| 2,878,486 | 3/1959 | Bartlett et al. ............... 4/110 |
| 3,306,515 | 2/1967 | Beaumont ................... 229/22 |
| 3,556,102 | 1/1971 | Davis . |
| 3,613,122 | 10/1971 | Gross et al. ............... 4/144.4 |
| 3,864,759 | 2/1975 | Horiuchi ...................... 4/110 |
| 3,964,111 | 6/1976 | Packer .......................... 4/110 |
| 3,995,329 | 12/1976 | Williams ...................... 4/110 |
| 4,023,216 | 5/1977 | Li .................................. 4/110 |
| 4,296,502 | 10/1981 | Bortle .......................... 4/114.1 |
| 4,528,703 | 7/1985 | Kraus ......................... 4/144.2 |
| 4,608,046 | 8/1986 | Towfigh ...................... 604/329 |
| 4,626,249 | 12/1986 | Hamey ....................... 604/329 |
| 4,681,573 | 7/1987 | McGovern et al. ......... 604/329 |
| 4,751,751 | 6/1988 | Reno ........................... 4/144.4 |
| 4,937,890 | 7/1990 | Tafur .......................... 4/144.4 |
| 5,408,703 | 4/1995 | Cicio .......................... 4/144.2 |

FOREIGN PATENT DOCUMENTS

| | | |
|---|---|---|
| 158602 | 10/1985 | European Pat. Off. . |
| 2232597 | 12/1990 | United Kingdom . |
| WO 82/02831 | 9/1982 | WIPO . |

*Primary Examiner*—Charles E. Phillips
*Attorney, Agent, or Firm*—Standley & Gilcrest

[57] ABSTRACT

A disposable female urination device having a main body portion with two openings. One opening is adapted to fit over a female vulva, while the other opening is used to discharge urine. The urination device of the present invention allows a female user to urinate while in the standing position.

17 Claims, 2 Drawing Sheets

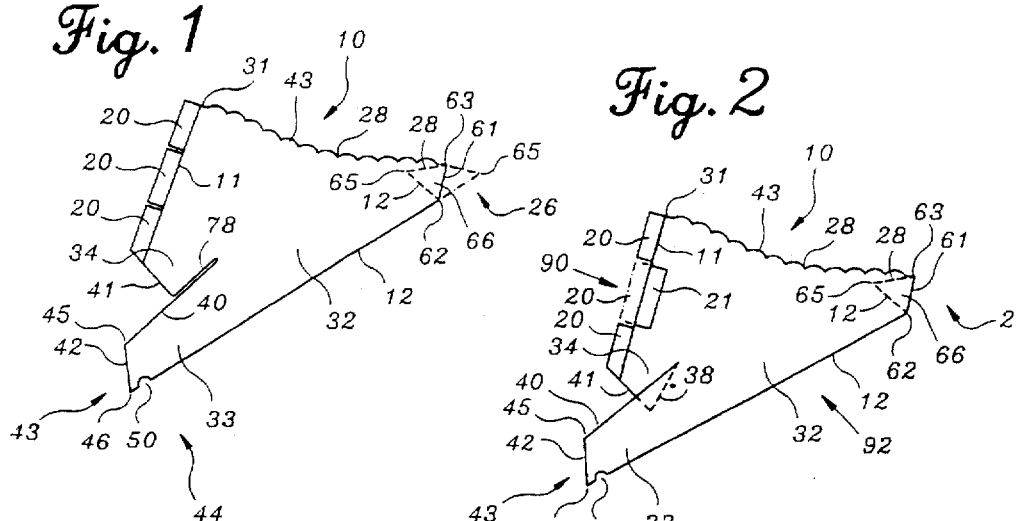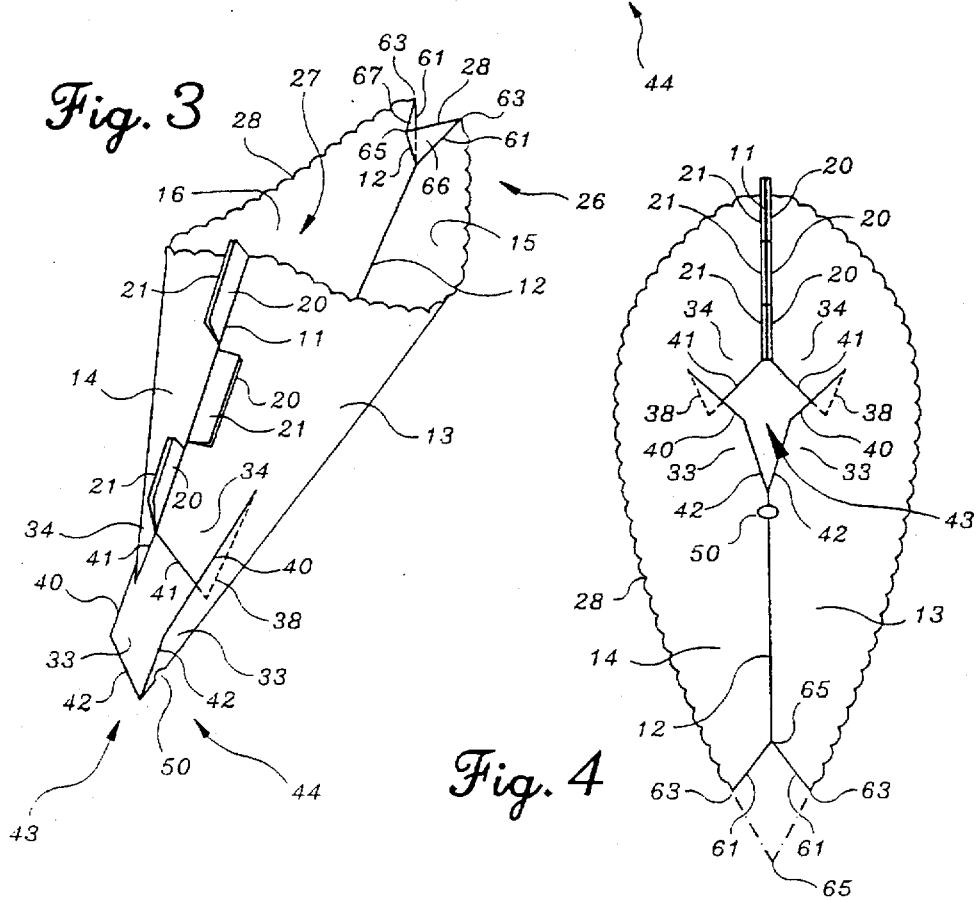

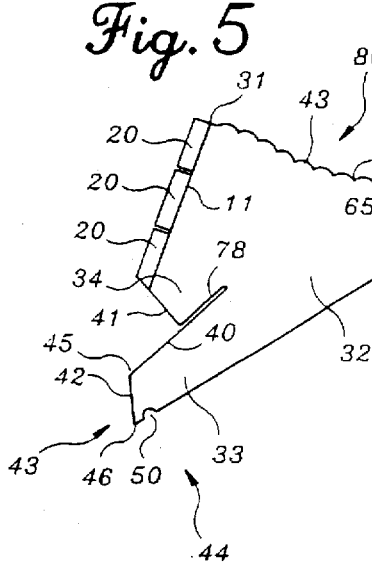
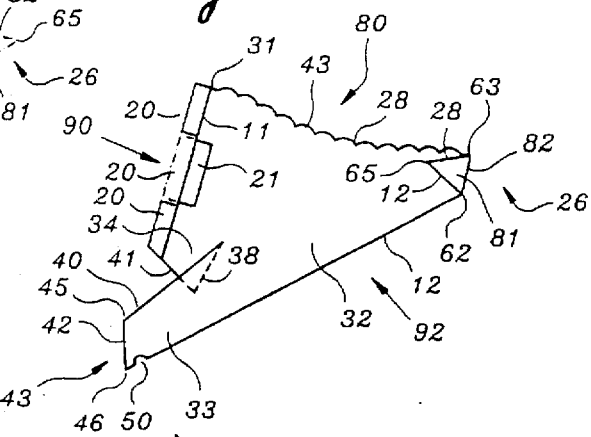
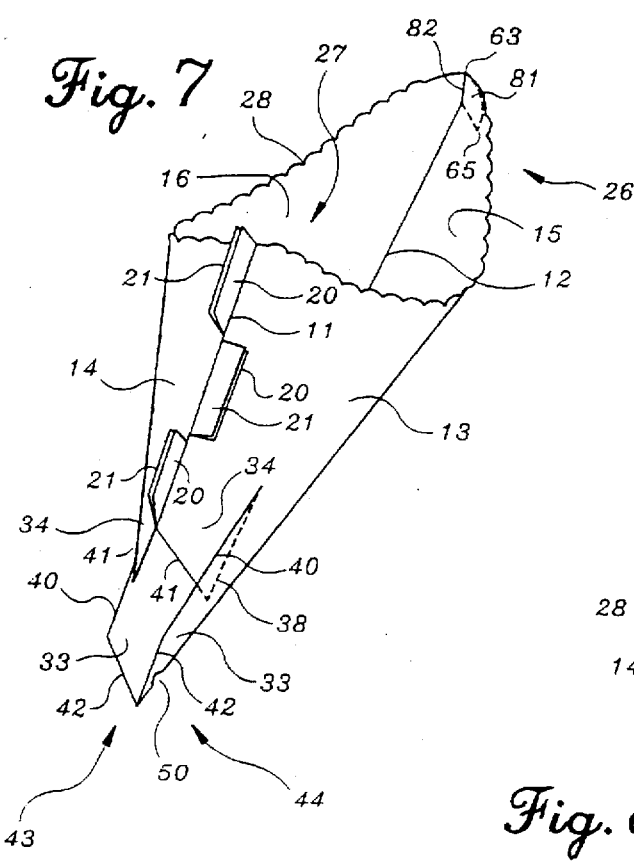
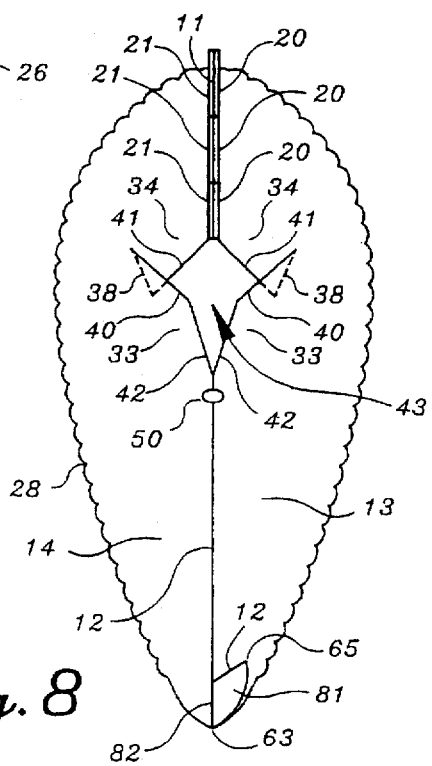

FEMALE URINATION AID

This application claims the benefit of U.S. Provisional Application No. 06/002,609 filed on Aug. 11, 1995.

BACKGROUND AND SUMMARY OF THE INVENTION

The present invention relates to female urination devices, and more particularly, to devices which allow a female to urinate from a standing position.

Public restrooms for women are often unclean and unsanitary. Particularly, the toilet seats in public restrooms are often dirty or otherwise in an unsanitary condition. Accordingly, many women are forced to squat above the toilet seat when using the restroom so as to avoid contact with the dirty toilet seat. This is a very uncomfortable and unpleasant way for a woman to urinate. Likewise, when camping or traveling, a woman's restroom may not be available, whereby a woman must squat, while holding her clothing out of the way, in order to urinate. Accordingly, there is a need for a female urinating device which is effective, relatively simple in construction, and easy to use.

The present invention provides a unique disposable device for assisting a female in urinating from a standing position and for directing the urine a suitable distance away the female. The device comprises: a first end having an opening for receiving urine from a female, the opening having a circumference which is contoured to fit around the outside of a woman's vulva (the circumference of the opening containing scallops or frills to enhance comfort and reduce the possibility of papercut injuries to the skin during use), a second end, opposite the first, having an opening for discharging the urine from the device, and a longitudinal crease extending from the first end to the second end.

In the preferred embodiment, the circumference has an anterior-most half and a posterior-most half in relation to a woman's body during use. A portion of the posterior-most half of the circumference may be creased and inverted, reversed, or overlapped in the anterior direction to comprise a posterior flow barrier wall, or crease, for preventing undesirable posterior urine run-off from the device.

As discussed above, the present invention is also comprised of a second end having an opening for discharging the urine from the device. The opening in the second end is preferably comprised of a top surface and a bottom surface wherein the bottom surface extends beyond the top surface to create an angled opening and first and second longitudinal creases extending from the first end to the second end.

In the preferred embodiment, the first and second longitudinal creases extend from the first end to the second end. The creases define first and second walls, each having an inside surface wherein the inside surface is coated with a moisture-resistant coating. The device may be split at its second end to comprise a lower v-shaped trough and an upper, inverted, v-shaped guide. The upper, inverted, v-shaped guide is preferably shorter in length than the lower trough, and acts as a guide to control fluid turbulence. A hole may be added at, or near, the end of the lower trough as a braking mechanism for preventing drips.

Additionally, in the preferred embodiment, the longitudinal crease of the first and second walls define a first and second row of symmetrically opposing flaps, each flap of the first row of flaps having an inside surface which is attached to the corresponding inside surface of the symmetrically opposing flap of the second row. The flaps join the first and second walls along a common edge as well as acting as a guide for the placement of a woman's fingers along the first longitudinal crease of the device during use.

It is the object of the present invention to provide a female urination device which allows a woman to urinate from a standing position and which is inexpensive and simple to use.

It is another object of the invention to provide a disposable female urination device to assist a female in urinating from a standing position and which may be stored in a folded condition.

It is another object of the invention to provide a female urination device which allows a woman to urinate from a standing position which is contoured to fit around a woman's vulva.

Other principal features and advantages of the invention will become apparent to those skilled in the art upon review of the following detailed description, claims, and drawings.

BRIEF DESCRIPTION OF THE DRAWINGS

Novel features and advantages of the present invention, in addition to those mentioned above, will become apparent to those skilled in the art from a reading of the following detailed description in conjunction with the accompanying drawings wherein similar reference characters refer to similar parts and in which:

FIG. 1 is a side view of the device of the present invention in a closed or flat configuration;

FIG. 2 is a side view of the device of the present invention in an open or usable configuration;

FIG. 3 is perspective view of the device of the present invention in an open or usable configuration;

FIG. 4 is an end view of the device of the present invention in an open or usable configuration;

FIG. 5 is a side view of another embodiment of the device of the present invention in a closed configuration;

FIG. 6 is a side view of the device of FIG. 5 in an open or usable configuration;

FIG. 7 is a perspective view of device of FIG. 6; and

FIG. 8 is an end view of the device of FIG. 7.

DESCRIPTION OF THE PREFERRED EMBODIMENTS

The preferred system herein described is not intended to be exhaustive or to limit the invention to the precise forms disclosed. They are chosen and described to explain the principles of the invention, and the application of the method to practical uses, so that others skilled in the art may practice the invention.

A female urination device 10 embodying the invention is illustrated in the drawings. The device 10 includes a first, or upper, longitudinal crease 11 and a second, or lower, longitudinal crease 12. The creases 11, 12 define first and second walls 13, 14. The walls 13, 14 may be made of any suitable water-absorbent paper, cardboard, or water dissolvable plastic-like film. The walls 13, 14 have inside surfaces 15, 16 which may be coated with a thin, moisture-resistant, coating which prevents the urine passing through the device 10 from effecting its structural integrity.

The device 10 is preferably stored in a flattened manner as illustrated in FIG. 1 such as would be the case if the device were stored in a package, dispensing machine, or the like. In order to get the device to an open or usable configuration, pressure is applied to the two creases 11, 12 with the thumb and index finger. This open, or usable, configuration is illustrated in FIG. 2.

The first wall 13 may include a first row of tabs 20 along the upper longitudinal crease 11. The opposing wall 14 may include a second row of tabs 21 along the upper longitudinal crease 11. The inner surfaces of the tabs 20 along the upper longitudinal crease 11 of the first wall 13 are glued, crimped, or otherwise attached, to the symmetrically opposing inner surface of respective tabs 21 along the upper longitudinal crease 11 of the second wall 14. The glued tabs 20, 21 bond the upper edges of the first and second walls 13, 14 along the first, or upper, longitudinal crease 11. Once joined, the crease 11 becomes a series of tabs (three tabs in the preferred embodiment) along the first, or upper, longitudinal crease 11. The joined tabs 20, 21 also function as a guide for the placement of the woman's thumb on the upper longitudinal crease 11 while holding the device in place during use. FIGS. 2–3 illustrate how the joined middle tabs 20, 21 are bent aside during use which allows the remaining tabs to act as posterior and anterior guides, respectively, between which a woman would place her thumb while holding the device 10 during use.

The device 10 has a first end 26 having a first, or large, opening 27. Once the device 10 has been opened, the device can be used by placing the first, or larger, opening 27 around the outside of the woman's vulva. This first opening 27 has a circumference 28 (or fringe) which has a posterior-most point 65 where the circumference 28 and the lower longitudinal crease 12 intersect. The first opening 27 also has an anterior-most point 31 where the circumference 28 and the upper longitudinal crease 11 intersect. The posterior-most point 65 and anterior-most point 31 along the circumference 28 of the larger opening 27 are preferably in direct relationship to the orientation of the woman's body during use of device 10. The first opening 27 may be comprised of any number of scallops or frills 43 which act as part of its circumference 28 to "soften" the edge of the first opening 17. These edges 28 lessen the likelihood of paper cut injuries when the device 10 is held in its operable position during use. These scallops, or frills, 43 may be of a size that is apparent to the human eye or, in the alternative, of a size and configuration that may be extremely fine and imperceptible to the unaided human eye. It should be noted that the circumference 28 of the first opening 27 is contoured to insure a tight and comfortable fit around the vulva when the device is held in place during use. This contour could be described as a "shallow cosinal curvature" when the device 10 viewed from either side in a flattened position. This contour or curvature of the first opening 27 also provides more comfort than if the end 26 merely had a U-shaped curvature (the U-shaped curvature would result in a point at the front and rear of the opening).

With the larger first opening 27 placed around the outside of the woman's vulva, the woman may urinate from a standing position. The device 10 is preferably placed around the vulva such that the lower longitudinal crease 12 is at the bottom of the device. In this position, the lower longitudinal crease 12 serves as a trough which will focus the urine into a stream form.

The present embodiment illustrated in FIGS. 1–4 establishes three uniquely different regions of the device; the main body 32, the lower v-shaped trough 33, and the upper inverted v-shaped guide 34. The lower longitudinal crease 12 not only establishes the bottom edge of the body 32 of the device, but it also establishes the bottom edge of the lower v-shaped trough 33. Conversely, the corresponding upper longitudinal crease 11 not only establishes the top edge of the body of the device 10, but it also establishes the top edge of the upper inverted v-shaped guide 34.

As the device 10 is squeezed open by applying opposing forces simultaneously at the upper and lower longitudinal creases 11, 12 in directions 90 and 92, the upper longitudinal crease 11 angles downward toward the lower longitudinal crease 12, and the upper inverted v-shaped guide 34 moves downward into the lower v-shaped trough 33 where it acts as a buffer against fluid turbulence.

As the device 10 is squeezed open, the two descending flanks 34, formed from a slit 78 in each of the walls 13, 14, move downward inside the two upper edges 40 defining the lower trough. The two leading edges of the upper guide 41 and the two leading edges of the lower trough 42 form the discharge, or second, opening 43.

The urine will travel down the device to the second end 44 and exit the device through the discharge opening 43. Although the discharge opening 43 may be of any suitable form, the discharge opening 43 is preferably angled such that the lower longitudinal crease 12 extends beyond the upper edges 40 of the lower trough. In other words, the discharge opening 43 has a top surface and a bottom surface. The bottom surface extends beyond the top surface such that the angle created by an imaginary line extending from the most forward edge 45 of the upper edges 40 of the lower trough to the most forward edge 46 of the lower longitudinal crease 12, with respect to the lower longitudinal crease 12, is less than 90 degrees (preferably is between 35 degrees and 85 degrees). This angled discharge opening prevents urine from "dribbling" out of the opening 43 and provides for a clean discharge of the urine a suitable distance away from the female and from the device 10. A small hole 50 may be added at or near the end of the lower trough, preferably in the lower longitudinal crease 12, as a braking mechanism against drips.

The present embodiment illustrated in FIGS. 1–4 also utilizes a posterior flow barrier whereby first and second walls 13, 14 each comprise a posterior crease 61 which traverses each of the first and second walls 13, 14 from a point 62 on the posterior half of the lower longitudinal crease 12 and extends to a point 63 on the posterior half of the circumference 28 of the large opening 27 which defines the upper edge of the same wall. The presence of the traversing posterior crease 61 in the first and second walls 13, 14, allows for a portion of the posterior half of the lower longitudinal crease 12 and a portion of the posterior half of the circumference 28 of the large opening 27 (including apex 65 representing the intersecting point of the lower longitudinal crease 12 with the circumference 28 of the large opening 27) to be inverted, or reversed, toward the anterior direction of the device 10. This inversion of the apex 65 creates first and second barrier walls 66, 67 which act as a barrier against undesirable posterior urine run-off from the device 10.

An alternative embodiment of the invention is illustrated in FIGS. 5–8. This alternative embodiment 80 operates a similar manner as the device 10 of the present invention illustrated in FIGS. 1–4.

As the device 80 is squeezed opened by applying opposing forces simultaneously at the upper and lower longitudinal creases 11, 12 in directions 90 and 92, the upper longitudinal crease 11 angles downward toward the lower longitudinal crease 12, and the upper inverted v-shaped guide 34 moves downward into the lower v-shaped trough 33 where it acts as a buffer against fluid turbulence.

As the device 80 is squeezed open, the two descending flanks 34, formed from a slit 78 in each of the walls 13, 14, move downward inside the two upper edges 40 defining the lower trough. The two leading edges of the upper guide 41 and the two leading edges of the lower trough 42 form the discharge opening 43.

The present embodiment 80 illustrated in FIGS. 5–8 also utilizes a posterior flow barrier whereby the first and second walls 13, 14 each comprise a posterior crease. The posterior crease traverses each of the first and second walls 13, 14 from a point 62 on the posterior half of the lower longitudinal crease 12 and extends to a point 63 on the posterior half of the circumference 28 of the large opening 27 which defines the upper edge of the same wall. The presence of the traversing posterior crease 61 in the first and second walls 13, 14 allows for a portion of the posterior half of the first and second walls 13, 14, a portion of the posterior half of large opening circumference 28, as well as a portion of the posterior half of lower longitudinal crease 12 (including apex 65 representing the intersecting point of the lower longitudinal crease 12 with circumference 18 of large opening 27) to be folded back in an overlapping fashion so that a portion of the surface of the posterior half of the first wall 13 folds back in the anterior direction of the device onto itself and is adhered, or otherwise attached, to the same. This overlapping anterior portion 81 of the first and second walls 13, 14 onto the first wall 13 creates a barrier crease 82 which acts as a barrier against undesirable posterior urine run-off from the device.

As the device is water absorbent, after use, the device 10 may be disposed of by throwing it in the trash or by throwing it in the toilet.

Since this device 10 may be constructed of water-absorbent paper and may be held together with a water-soluble glue, the device can be disposed by flushing it down a toilet (as the device will quickly soften once it touches the water). The water-soluble glue allows the device to disassemble in water, further reducing its structural integrity.

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A disposable female urination device, comprising:
    a main body portion, having a first and second end, said first end having a first opening, said second end having a second opening, said second opening located opposite from said first opening, wherein a perimeter of said first opening is comprised of frills for softening the edges of said first opening;
    wherein said first opening is adapted to receive urine from a female user;
    wherein urine from said female user is discharged from said second opening; and
    wherein said disposable urinating device allows a female user to urinate while in the standing position.

2. A female urination device according to claim 1, wherein said main body portion is comprised of:
    an upper longitudinal crease extending from said first end to said second end; and
    a lower longitudinal crease extending from said first end to said second end.

3. A female urination device according to claim 2, wherein said main body portion is comprised of:
    a lower trough, defined by said lower longitudinal crease; and
    an upper inverted guide defined by said a upper longitudinal crease.

4. A female urination device according to claim 3, wherein said main body portion is further comprised of:
    a first wall;
    a second wall; and
    wherein said first and second walls are defined by and attached at said upper and lower longitudinal creases.

5. A female urination device according to claim 4, wherein said walls may be made from any suitable water-absorbent paper, cardboard, or water dissolvable plastic-like film.

6. A female urination device according to claim 4, wherein said first and second walls have inner surfaces coated with a thin, moisture-resistant, coating for preventing urine from passing through said walls.

7. A female urination device according to claim 4, wherein said first wall has a first row of tabs along said upper longitudinal crease; wherein said second wall has a second row of tabs along said upper longitudinal crease; and wherein said first and second row of tabs are joined together along said upper longitudinal crease bonding the first and second walls along said upper longitudinal crease.

8. A female urination device according to claim 7, wherein said joined first and second row of tabs function as a guide for the placement of the user's thumb on said upper longitudinal crease while holding said device during use.

9. A female urination device according to claim 8, wherein said device may be stored in a flattened condition; and
    wherein said device is opened by applying simultaneous pressure to said upper and lower longitudinal creases.

10. A female urination device according to claim 8, wherein said first opening has a circumference having a posterior-most point where said circumference and lower longitudinal crease intersects; and wherein said first opening has an anterior-most point where said circumference and upper longitudinal crease intersects.

11. A female urination device according to claim 10, wherein a posterior flow barrier is formed by inverting a portion of the posterior portion of said circumference and said lower longitudinal crease toward said anterior portion of said device.

12. A female urination device according to claim 10, wherein said circumference is in the shape of a shallow cosinal curvature.

13. A female urination device according to claim 4, wherein said lower longitudinal crease contains a small hole near said second opening for preventing against urine dripping.

14. A female urination device according to claim 4, wherein said second opening is angled so that said second opening prevents urine from dribbling out of the opening and provides for a clean discharge of the urine to a suitable distance from said device.

15. A disposable female urination device, comprising:
    a main body portion, having a first and second end, said first end having a first opening; said second end having a second opening, said second opening located opposite from said first and from said first opening;
    a posterior flow barrier for preventing urine run-off from said first opening;

wherein said first opening is adapted to cover a vulva of a female user;

wherein urine from said female user is discharged from said second opening;

wherein said main body portion is comprised of:
an upper longitudinal crease extending from said first end to said second end; and
a lower longitudinal crease extending from said first end to said second end,
a lower trough defined by said lower longitudinal crease;
an upper inverted guide defined by said upper longitudinal crease;
a first wall;
a second wall;

wherein said first and second walls are defined and attached at said upper and lower longitudinal creases;

wherein said walls may be made from any suitable water-absorbent paper, cardboard, or water dissolvable plastic-like film;

wherein said first and second walls have inner surfaces coated with a thin, moisture-resistant, coating for preventing urine from passing through said walls;

wherein said first wall has a first row of tabs along said upper longitudinal crease;

wherein said second wall has a second row of tabs along said upper longitudinal crease;

wherein said first and second row of tabs are attached together along said upper longitudinal crease bonding the first and second walls along said upper longitudinal crease;

wherein said joined first and second row of tabs function as a guide for the placement of the user's thumb while holding said device during use;

wherein said device may be stored in a flattened condition;

wherein said first opening has a circumference having a posterior-most point where said circumference and said lower longitudinal crease intersects;

wherein said first opening has an anterior-most point where said circumference and said upper longitudinal crease intersects;

wherein said circumference of said first opening is comprised of a plurality of frills for softening the edges of said first opening;

wherein said posterior flow barrier is formed by inverting a portion of the posterior-most portion of said circumference and said lower longitudinal crease toward said anterior-most portion of said device;

wherein said second opening is angled so that said second opening prevents urine from dribbling out of said second opening and provides for a clean discharge of the urine a suitable distance from said device;

wherein said lower longitudinal crease contains a small hole near said second opening for preventing against urine dripping; and wherein said disposable urinating device allows a female user to urinate while in the standing position.

16. A disposable female urination device, comprising:

a main body portion, having a first and second end, said first end having a first opening, said second end having a second opening, said second opening located opposite from said first opening, wherein said main body portion is comprised of an upper longitudinal crease extending from said first end to said second end, a lower longitudinal crease extending from said first end to said second end, a first wall, a second wall, and wherein said first and second walls are joined at said upper and lower longitudinal creases;

wherein said first wall has a first row of tabs, wherein said second wall has a second row of tabs, and wherein corresponding tabs of said first and second rows of tabs are bonded together joining the first and second walls along said upper longitudinal crease, each row comprising at least a first, second and third tab;

wherein said first opening is adapted to receive urine from a female user;

wherein urine from said female user is discharged from said second opening; and wherein said disposable urinating device allows a female user to urinate while in the standing position and disposition of said second tab in an opposite direction of said first and third tabs provided for posterior and anterior guides for the user's thumb.

17. A device according to claim 16, wherein said first and second rows of tabs are each comprised of three tabs.

* * * * *

UNITED STATES PATENT AND TRADEMARK OFFICE
CERTIFICATE OF CORRECTION

PATENT NO. : 5,742,948
DATED : April 28, 1998
INVENTOR(S) : William H. Cicio

It is certified that error appears in the above-identified patent and that said Letters Patent is hereby corrected as shown below:

In column 1, line 26, before the word "the, please add the word -- from --.

In column 3, line 36, please delete the number "17" and replace it with -- 27 --.

Signed and Sealed this

Twenty-seventh Day of October, 1998

Attest:

BRUCE LEHMAN

*Attesting Officer*         *Commissioner of Patents and Trademarks*